US006946441B2

(12) United States Patent
Long et al.

(10) Patent No.: US 6,946,441 B2
(45) Date of Patent: *Sep. 20, 2005

(54) INHIBITION OF HISTONE DEACETYLASE AS A TREATMENT FOR CARDIAC HYPERTROPHY

(75) Inventors: Carlin Long, Denver, CO (US); Eric N. Olson, Dallas, TX (US); Michael Bristow, Cherry Hills Village, CO (US); Timothy A. McKinsey, Broomfield, CO (US)

(73) Assignees: Regents of the University of Colorado, A Body Corporation, Boulder, CO (US); The Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/801,985

(22) Filed: Mar. 16, 2004

(65) Prior Publication Data

US 2004/0186049 A1 Sep. 23, 2004

Related U.S. Application Data

(63) Continuation of application No. 10/256,221, filed on Sep. 26, 2002, now Pat. No. 6,706,686.
(60) Provisional application No. 60/334,041, filed on Oct. 31, 2001, and provisional application No. 60/325,311, filed on Sep. 27, 2001.

(51) Int. Cl.[7] .................... A61K 38/00; A61K 31/47; A61K 31/44; A61K 31/335; A61K 31/165
(52) U.S. Cl. .................... 514/10; 514/307; 514/357; 514/475; 514/618; 514/654
(58) Field of Search .................... 514/10, 307, 357, 514/475, 618, 654

(56) References Cited

U.S. PATENT DOCUMENTS

| | | | | |
|---|---|---|---|---|
| 6,706,686 B2 | * | 3/2004 | Long et al. .................... | 514/10 |
| 2002/0061860 A1 | | 5/2002 | Li et al. .................... | 514/44 |
| 2002/0065282 A1 | | 5/2002 | Georges et al. .................... | 514/238.2 |
| 2002/0103192 A1 | | 8/2002 | Curtin et al. .................... | 514/227.8 |

FOREIGN PATENT DOCUMENTS

| | | |
|---|---|---|
| EP | 1170008 | 1/2002 |
| EP | 1174438 | 1/2002 |
| JP | 2001/348340 | 12/2001 |
| WO | WO 00/23112 | 4/2000 |
| WO | WO 00/71703 | 11/2000 |
| WO | WO 01/14581 | 3/2001 |
| WO | WO 01/16106 | 3/2001 |
| WO | WO 01/17514 | 3/2001 |
| WO | WO 01/18045 | 3/2001 |
| WO | WO 01/38322 | 5/2001 |
| WO | WO 01/42437 | 6/2001 |
| WO | WO 01/70675 | 9/2001 |
| WO | WO 02/26696 | 4/2002 |
| WO | WO 02/26703 | 4/2002 |
| WO | WO 02/30879 | 4/2002 |
| WO | WO 02/46129 | 6/2002 |
| WO | WO 02/46144 | 6/2002 |
| WO | WO 02/50285 | 6/2002 |
| WO | WO 02/051842 | 7/2002 |

OTHER PUBLICATIONS

Cecil Textbook of Medicine, Goldman et al. (eds.), published 2000 by W.B. Saunders Company (PA), p. 217.*

Bates et al., "A phase I study of FR901228(Depsipeptide), a histone deacetylase inhibitor," *American Society of Clinical Oncology Meeting 1999 Abstract*, Abstract # 693, 1999, printed from www.medespace.com/cancero/doc/asco/1999/nouvdro/m_693.htm, May 7, 2001.

Butler et al., "Inhibition of transformed cell growth and induction of cellular differentiation by pyroxamide, an inhibitor of histone deacetylase," *Clin. Cancer Res.*, 7:962–970, 2001.

Butler et al., "Suberoylanilide hydroxamic acid, an inhibitor of histone deacetylase, suppresses the growth of prostate cancer cells in vitro and in vivo," *Cancer Res.*, 60:5165–5170, 2000.

Coffey et al., "The histone deacetylase inhibitor, CBHA, inhibits growth of human neuroblastoma xenografts in vivo, alone and synergistically with all–trans retinoic acid," *Cancer Res.*, 61:3591–3594, 2001.

Furumai et al., "FK228 (Depsipeptide) as a natural prodrug that inhibits class I histone deacetylases," *Cancer Res.*, 62:4916–4921, 2002.

Gottlicher et al., "Valproic acid defines a novel class of HDAC inhibitors inducing differentiation of transformed cells," *EMBO J.*, 20:6969–6978, 2001.

Han et al., "Apicidin, a histone deacetylase inhibitor, inhibits proliferation of tumor cells via induction of p21$^{WAF1/Cip1}$ and gelsolin," *Cancer Research*, 60:6068–6074, 2000.

Haq, "Glycogen synthase kinase–3β is a negative regulator of cardiomyocyte hypertrophy," *J. Cell Biology*, 151:117–129, 2000.

Hinnebusch et al., "The effects of short–chain fatty acids on human colon cancer cell phenotype are associated with histone hyperacetylation," *J. Nutr.*, 132:1012–1017, 2002.

(Continued)

*Primary Examiner*—Raymond J. Henley, III
(74) *Attorney, Agent, or Firm*—Fulbright & Jaworski

(57) ABSTRACT

The present invention provides for methods of treating and preventing cardiac hypertrophy. Class II HDACs, which are known to participate in regulation of chromatin structure and gene expression, have been shown to have beneficial effects on cardiac hypertrophy. Surprisingly, the present invention demonstrates that HDAC inhibitors inhibit cardiac hypertrophy by inhibiting fetal cardiac gene expression and interfering with sarcomeric organization.

10 Claims, 7 Drawing Sheets

OTHER PUBLICATIONS

Hoffmann et al., "Fluorescence–labeled octapeptides as substrates for histone deacetylase," *Bioconjugate Chem.*, 12:51–55, 2001.

Itazaki et al., "Isolation and structural elucidation of new cyclotetrapeptides, trapoxins A and B, having detransformation activities as antitumor agents," *J Antibiot (Tokyo)*, 43(12):1524–1532, 1990.

Jung et al., "Amide analogues of trichostatin A as inhibitors of histone deacetylase and inducers of terminal cell differentiation," *J. Med. Chem.*, 42:4669–4679, 1999.

Jung et al., "Analogues of trichostatin A and trapoxin B as histone deacetylase inhibitors," *Bioorganic & Medicinal Chemistry Letters*, 7:1655–1658, 1997.

Jung et al., "Structure–activity data on inhibitors of histone deacetylase–in vivo enzyme inhibition of differentiation and inhibition of proliferation in leukemic cells," *Clin. Cancer Res., Suppl.* 6: Abstract #336, 2000.

Jung, "Inhibitors of histone deacetylase as new anticancer agents," *Curr. Med. Chem.*, 8:1505–1511, 2001.

Katoh et al., "MEF2B is a component of a smooth muscle–specific complex that binds an A/T–rich element important for smooth muscle myosin heavy chain gene expression," *J. Biol. Chem.*, 273:1511–1518, 1998.

Kim et al., "Oxamflatin is a novel antitumor compound that inhibits mammalian histone deacetylase," *Oncogene*, 18:2461–2470, 1999.

Kitazono et al., "Low concentrations of the histone deacetylase inhibitor, depsipeptide (FR901228), increase expression of the $NA^-/I^-$ symporter and iodine accumulation in poorly differentiated thyroid carcinoma cells," *J. Clinical Endoc. Metabol.*, 86(7):3430–3435, 2001.

Komastsu et al., "Cyclic hydroxamic–acid–containing peptide 31, a potent synthetic histone deacetylase inhibitor with antitumor activity," *Cancer Res.*, 61:4459–4466, 2001.

Kramer et al., "Histone deacetylase as a therapeutic target," *Trends in Endoc. Metabolism*, 12(7):294–300, 2001.

Lu et al., "Signal–dependent activation of the MEF2 transcription factor by dissociation from histone deacetylases," *Proc. Natl Acad. Sci. USA*, 97:4070–4075, 2000.

Mai et al., "Binding mode analysis of 3–(4–benzoyl–1–methyl–1H–2–pyrroly)–N–hydroxyy–2–propenamide: a new synthetic histone deacetylase inhibitor inducing histone hyperacetylation, growth inhibition, and terminal cell differentiation," *J. Med. Chem.*, 45:1778–1784, 2002.

Marks et al., "Histone deacetylase inhibitors: inducers of differentiation or apoptosis of transformed cells," *J. Natl. Cancer Inst.*, 92(15):1210–1216, 2000.

Marks et al., "Inhibitors of histone deacetylase are potentially effective anticancer agents," *Clin. Cancer Res.*, 7:759–760, 2001.

Massa et al, "3–(4–Aroyl–1H–pyrrol–2–yl)–N–hydroxy–2–propenamides, a new class of synthetic histone deacetylase inhibitors," *J. Med. Chem.*, 44:2069–2072, 2001.

Nicol et al., "Activated MEK5 induces serial assembly of sarcomeres and eccentric cardiac hypertrophy," *The EMBO J.*, 20(11):2757–2767, 2001.

Patrone et al., "Up regulation of the RET gene expression by histone deacetylase inhibitor sodium butyrate: hints to the gene physiologic regulation and applications for mutations screening," *50th Annual Meeting of the American Society of Human Genetics, Abstracts*, Program No. 1047, 2000.

Salminen et al., "Neuronal apoptosis induced by histone deacetylase inhibitors," *Brain Res. Mol. Brain Res.*, 61:203–206, 1998.

Saunders et al., "Histone deacetylase inhibitors as potential anti–skin cancer agents," *Cancer Res.*, 59–399–409, 1999.

Skaletz–Rorowski et al., "The histone deacetylase inhibitors, trichostatin A and the new synthetic inhibitor M232, suppress the proliferation of corornary smooth muscle cells," *Eur. Heart J.*, Abstract Suppl., 21:272, Abstract #P1551, Aug./Sep. 2000.

Su et al., "A novel histone deacetylase inhibitor identified by high–throughput transcriptional screening of a compound library," *Cancer Res.*, 60:3137–3142, 2000.

Takahashi et al., "Selective inhibition of IL–2 gene expression by trichostatin A, a potent inhibitor of mammalian histone deacetylase," *Antibiotics*, 49:453–457, 1996.

Taunton et al., "A mammalian histone deacetylase related to the yeast transcriptional regulator Rpd3p," *Science*, 272:408–411, 1996.

Ueda et al., "FR901228, a novel antitumor bicyclic depsipeptide produced by Chromobacterium violaceum No. 968. I. Taxonomy, fermentation, isolation, physico–chemical and biological properties, and antitumor activity," *J Antibiot (Tokyo)*, 47(3):301–310, 1994.

Vigushin et al., "Histone deacetylase inhibitors in cancer treatment," *Anticancer Drugs*, 13:1–13, 2002.

Vigushin et al., "Trichostatin A is a histone deacetylase inhibitor with potent antitumor activity against breast cancer in vivo," *Cancer Res.*, 5(Suppl), Abstract #239, 1999.

Vigushin et al., "Trichostatin A is a histone deacetylase inhibitor with potent antitumor activity against breast cancer in vivo," *Clinical Cancer Res.*, 7:971–976, 2001.

Yamano et al., "Amplification of transgene expression in vitro and in vivo using a novel inhibitor of histone deacetylase," *3rd Annual Meeting of the American Society of Gene Therapy*, Program No. 10, 2000.

Yamano et al., "Amplification of transgene expression in vitro and in vivo using a novel inhibitor of histone deacetylase," *Mol. Ther., Amer. Society of Gene Ther.*, 1(5):S20, Abstract #10, 2000.

Yamano et al., "Construction and function of a recombinant adeno–associated virus encoding human interleukin–10," *Mol. Ther., Amer. Society of Gene Ther.*, 1(5):S276, Abstract #764, 2000.

* cited by examiner

* $P<0.05$ vs Control,
† $P<0.05$ vs PE,
‡ $P<0.05$ vs TSA (-).

* $P<0.05$ vs Vector,
† $P<0.05$ vs Vector+PE.

INHIBITION OF HISTONE DEACETYLASE AS A TREATMENT FOR CARDIAC HYPERTROPHY

The present invention claims benefit of priority to and is a continuation of U.S. Ser. No. 10/256,221, filed Sep. 26, 2002, now issued as U.S. Pat. No. 6,706,686, which claims priority to U.S. Provisional Ser. Nos. 60/325,311, filed Sep. 27, 2001, and 60/334/041, filed Oct. 31, 2001, the entire contents of which are hereby incorporated by reference without reservation.

The government owns rights in the present invention pursuant to grant number NIH RO1 HL61544 from the National Institutes of Health.

BACKGROUND OF THE INVENTION

1. Field of the Invention

The present invention relates generally to the fields of developmental biology and molecular biology. More particularly, it concerns gene regulation and cellular physiology in cardiomyocytes. Specifically, the invention relates to the use of HDAC inhibitors to treat cardiac hypertrophy and heart failure.

2. Description of Related Art

Cardiac hypertrophy in response to an increased workload imposed on the heart is a fundamental adaptive mechanism. It is a specialized process reflecting a quantitative increase in cell size and mass (rather than cell number) as the result of any or a combination of neural, endocrine or mechanical stimuli. Hypertension, another factor involved in cardiac hypertrophy, is a frequent precursor of congestive heart failure. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy will be beneficial in the treatment of heart disease resulting from a various stimuli.

A family of transcription factors, the myocyte enhancer factor-2 family (MEF2), are involved in cardiac hypertrophy. For example, a variety of stimuli can elevate intracellular calcium, resulting in a cascade of intracellular signaling systems or pathways, including calcineurin, CAM kinases, PKC and MAP kinases. All of these signals activate MEF2 and result in cardiac hypertrophy. However, it is still not completely understood how the various signal systems exert their effects on MEF2 and modulate its hypertrophic signaling. It is known that certain histone deacetylase proteins, HDAC 4, HDAC 5, HDAC 7, HDAC 9, and HDAC 10, are involved in modulating MEF2 activity.

Eleven different HDACs have been cloned from vertebrate organisms. All share homology in the catalytic region. Histone acetylases and deacetylases play a major role in the control of gene expression. The balance between activities of histone acetylases, usually called acetyl transferases (HATs), and deacetylases (HDACS) determines the level of histone acetylation. Consequently, acetylated histones cause relaxation of chromatin and activation of gene transcription, whereas deacetylated chromatin is generally transcriptionally inactive. In a previous report, the inventors' laboratory demonstrated that HDAC 4 and 5 dimerize with MEF2 and repress the transcriptional activity of MEF2 and, further, that this interaction requires the presence of the N-terminus of the HDAC 4 and 5 proteins. McKinsey et al. (2000a,b).

In a distinct context, recent research has also highlighted the important role of HDACs in cancer biology. In fact, various inhibitors of HDACs are being tested for their ability to induce cellular differentiation and/or apoptosis in cancer cells. Marks et al. (2000). Such inhibitors include suberoylanilide hydroxamic acid (SAHA) (Butler et al., 2000; Marks et al., 2001); m-carboxycinnamic acid bis-hydroxamide (Coffey et al., 2001); and pyroxamide (Butler et al., 2001). These studies have been summarized as indicating "that the hydroxamic acid-based HPCs, in particular SAHA and pyroxamide—are potent inhibitors of HDAC in vitro and in vivo and induce growth arrest, differentiation, or apoptotic cell death of transformed cells . . . [and thus] are lead compounds among the family of hydroxamic acid-based HPCs and are currently in phase I clinical trials." Marks et al. (2000). To date, no reports on the effects of HDAC inhibitors on muscle cell hypertrophy and response to stress have been reported.

SUMMARY OF THE INVENTION

Thus, in accordance with the present invention, there is provided a method of treating pathologic cardiac hypertrophy and heart failure comprising (a) identifying a patient having cardiac hypertrophy; and (b) administering to the patient a histone deacetylase inhibitor. Administering may comprise intravenous, oral, transdermal, sustained release, suppository, or sublingual administration. The method may further comprise administering a second therapeutic regimen, such as a beta blocker, an iontrope, diuretic, ACE-I, AII antagonist or $Ca^{++}$-blocker. The second therapeutic regimen may be administered at the same time as the histone deacetylase inhibitor, or either before or after the histone deacetylase inhibitor. The treatment may improve one or more symptoms of cardiac failure such as providing increased exercise capacity, increased blood ejection volume, left ventricular end diastolic pressure, pulmonary capillary wedge pressure, cardiac output, cardiac index, pulmonary artery pressures, left ventricular end systolic and diastolic dimensions, left and right ventricular wall stress, wall tension and wall thickness, quality of life, disease-related morbidity and mortality.

In yet another embodiment, there is provided a method of preventing pathologic cardiac hypertrophy and heart failure comprising (a) identifying a patient at risk of developing cardiac hypertrophy; and (b) administering to the patient a histone deacetylase inhibitor. Administration may comprise intravenous, oral, transdermal, sustained release, suppository, or sublingual administration. The patient at risk may exhibit one or more of long standing uncontrolled hypertension, uncorrected valvular disease, chronic angina and/or recent myocardial infarction.

In accordance with the preceding embodiments, the histone deacetylase inhibitor may be any molecule that effects a reduction in the activity of a histone deacetylase. This includes proteins, peptides, DNA molecules (including antisense), RNA molecules (including RNAi and antisense) and small molecules. The small molecules include, but are not limited to, trichostatin A, trapoxin B, MS 275-27, m-carboxycinnamic acid bis-hydroxamide, depudecin, oxamflatin, apicidin, suberoylanilide hydroxamic acid, Scriptaid, pyroxamide, 2-amino-8-oxo-9,10-epoxy-decanoyl, 3-(4-aroyl-1H-pyrrol-2-yl)-N-hydroxy-2-propenamide and FR901228. Additionally, the following references describe histone deacetylase inhibitors which may be selected for use in the current invention: AU 9,013,101; AU 9,013,201; AU 9,013,401; AU 6,794,700; EP 1,233,958; EP 1,208,086; EP 1,174,438; EP 1,173,562; EP 1,170,008; EP 1,123,111; JP 2001/348340; U.S. 2002/103192; U.S. 2002/65282; U.S. 2002/61860; WO 02/51842;

WO 02/50285; WO 02/46144; WO 02/46129; WO 02/30879; WO 02/26703; WO 02/26696; WO 01/70675; WO 01/42437; WO 01/38322; WO 01/18045; WO 01/14581; Furumai et al. (2002); Hinnebusch et al. (2002); Mai et al. (2002); Vigushin et al. (2002); Gottlicher et al. (2001); Jung (2001); Komatsu et al. (2001); Su et al. (2000).

In still another embodiment, there is provided a method of identifying inhibitors of cardiac hypertrophy comprising (a) providing a histone deacetylase inhibitor; (b) treating a myocyte with the histone deacetylase inhibitor; and (c) measuring the expression of one or more cardiac hypertrophy parameters, wherein a change in the one or more cardiac hypertrophy parameters, as compared to one or more cardiac hypertrophy parameters in a myocyte not treated with the histone deacetylase inhibitor, identifies the histone deacetylase inhibitor as an inhibitor of cardiac hypertrophy. The myocyte may be subjected to a stimulus that triggers a hypertrophic response in the one or more cardiac hypertrophy parameters, such as expression of a transgene or treatment with a drug.

The one or more cardiac hypertrophy parameters may comprise the expression level of one or more target genes in the myocyte, wherein the expression level of the one or more target genes is indicative of cardiac hypertrophy. The one or more target genes may be selected from the group consisting of ANF, α-MyHC, β-MyHC, α-skeletal actin, SERCA, cytochrome oxidase subunit VIII, mouse T-complex protein, insulin growth factor binding protein, Tau-microtubule-associated protein, ubiquitin carboxyl-terminal hydrolase, Thy-1 cell-surface glycoprotein, or MyHC class I antigen. The expression level may be measured using a reporter protein coding region operably linked to a target gene promoter, such as luciferase, β-gal or green fluorescent protein. The expression level may be measured using hybridization of a nucleic acid probe to a target mRNA or amplified nucleic acid product.

The one or more cardiac hypertrophy parameters also may comprise one or more aspects of cellular morphology, such as sarcomere assembly, cell size, or cell contractility. The myocyte may be an isolated myocyte, or comprised in isolated intact tissue. The myocyte also may be a cardiomyocyte, and may be located in vivo in a functioning intact heart muscle, such as functioning intact heart muscle that is subjected to a stimulus that triggers a hypertrophic response in one or more cardiac hypertrophy parameters. The stimulus may be aortic banding, rapid cardiac pacing, induced myocardial infarction, or transgene expression. The one or more cardiac hypertrophy parameters comprises right ventricle ejection fraction, left ventricle ejection fraction, ventricular wall thickness, heart weight/body weight ratio, or cardiac weight normalization measurement. The one or more cardiac hypertrophy parameters also may comprise total protein synthesis.

In still yet another embodiment, there is provided a method of identifying inhibitors of cardiac hypertrophy comprising (a) providing at least one class I and one class II histone deacetylase; (b) contacting the histone deacetylases with a candidate inhibitor substance; and (c) measuring the activity of the histone deacetylases, wherein a greater decrease in class I histone deacetylase activity than class II histone deacetylase activity identifies the candidate inhibitor substance as an inhibitor of cardiac hypertrophy. The histone deacetylases may be purified away from whole cells or located in an intact cell. The cell may be a myocyte, such as a cardiomyocyte. Measuring HDAC activity may comprise measuring release of a labeled acetyl group from a histone. The label may be a radiolabel, a fluorescent label or a chromophore.

The class I histone deacetylase may be HDAC1, HDAC2, HDAC3, or HDAC 8. The class II histone deacetylase may be HDAC4, HDAC5, HDAC6, HDAC7, HDAC9, or HDAC 10. The activity of more than one class I histone deacetylase may be measured. The activity of more than one class II histone deacetylase may be measured. The activity of more than one class I histone deacetylase and more than one class II histone deacetylase may be measured. The candidate inhibitor substance may have inhibitory activity against at least one class I histone deacetylase and have no activity against at least one class II histone deacetylase. The candidate inhibitor substance may have inhibitory activity against multiple class I histone deacetylases and have no activity against multiple class II histone deacetylases. The candidate inhibitor substance may have inhibitory activity against at least one class I histone deacetylase that is at least two-fold greater than its inhibitory activity against at least one class II histone deacetylase. The candidate inhibitor substance may have inhibitory activity against at least one class I histone deacetylase that is at least five-fold greater than its inhibitory activity against at least one class II histone deacetylase.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) The ANF promoter is minimally active in unstimulated cardiomyocytes. The addition of HDAC inhibitors does not induce ANF promoter activity. Addition of phenylphrine activated the ANF promoter, but co-treatment of cardiomyoyctes with phenylephrine and a HDAC inhibitor (TSA (85 nM), NaBut (5 mM), or HC-toxin (5 ng/ml)) prevented the activation of the ANF promoter by phenylphrine (100 μM). (FIG. 3B) Lac Z expression by the constitutive promoter CMV. Treatment with HDAC inhibitors augmented CMV activity with and without phenylephrine co-treatment. (FIGS. 3C and 3D) The graphs show the measurements of adenylate kinase activity remains constant in the medium after X hours of culturing cardiomyocytes in the absence or presence of hypertrophic stimulants FBS, PE or ET-1.

(FIG. 4A) Graph shows the summation of several dot blot experiments (n=4). As in the transfection experiments, phenylephrine (100 □M) induces ANF expression over three-fold. Treatment with HDAC inhibitors (TSA 85 nM; sodium butyrate, 5 mM; HC-toxin 5 ng.ml) blocks the accumulation of ANF message. (FIGS. 4B and 4C) The graphs show a reduction of the chemiluminent detection of ANF in the culture medium with increasing concentrations of the HDAC inhibitors TSA (FIG. 4B) and sodium butyrate (FIG. 4C) when co-cultured with the hypertrophic stimulants FBS, PE or ET-1.

(FIG. 5A) Graph shows fold changes in αSK-actin expression by phenylephrine and the lack of gene activation in TSA-treated samples. (FIG. 5B) Graph shows the fold changes of αMyHC and βMyHC RNA expression. Phenylephrine treatment induces the activation of βMyHC expression (fetal gene) in cardiomyocytes; whereas, phenylephrine alone does not active the αMyHC gene, the adult isoform. Treatment with TSA prevented the activation of βMyHC but stimulated the expression of αMyHC. The graphs represent three or more independent experiments FIG. 6. The effects of TSA treatment on the reorganization of the sarcomeres and protein synthesis. Graphs of the measurements of S6 ribosome protein in cardiomyocytes shows that phenylephrine and serum increases protein synthesis in cardiomyocytes. Treatment of cardiomyocytes with TSA does not alter this increase after 6 hours (graphs on left). The graphs on the right show the content of S6 ribosome protein in cardiomyocytes after 24 hours co-treatment with PE and increasing concentrations of TSA or with serum and increasing concentrations of TSA.

(FIG. 7A) Three genes were up-regulated by phenylephrine and down-regulated by TSA. (FIG. 7B) Four genes were inactivated by phenylephrine and activated by TSA (results from one phenylephrine chip, two phenylephrine/TSA chips, and one TSA chip.)

DESCRIPTION OF ILLUSTRATIVE EMBODIMENTS

Figure 1A:
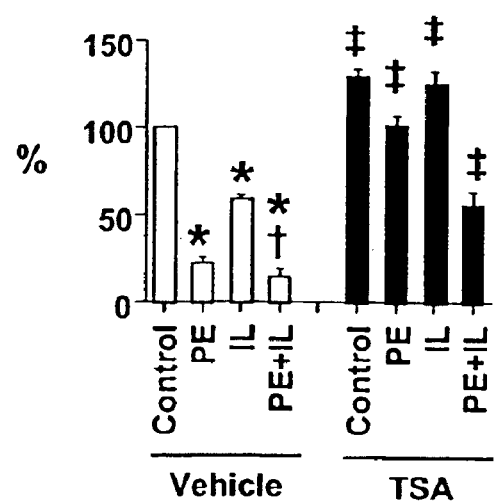
FIGS. 1A–C. TSA alters agonist-induced gene repression. Cultured cardiac myocytes were treated with PE (20 μmol/L) or IL-1 (1 ng/mL) for 48 hrs. TSA (30 nmol/L) was added 30 min. prior to treatment with PE or IL-1. Myocyte-specific mRNA expression (SERCA2a (FIG. 1A), αMyHC (FIG. 1B), βMyHC (FIG. 1C) was assayed in 5 μg total RNA by RNase protection assay. Mean data are from 4 cultures, and are presented as % of control after normalization to GAPDH signal.

Heart failure is one of the leading causes of morbidity and mortality in the world. In the U.S. alone, estimates, indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familiar dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including DCM, are significant public health problems.

As cardiomyopathy itself typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses, the symptoms progress as well. Patients with dilated cardiomyopathy also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

During attempts to identify and stabilize the underlying cause of the cardiomyopathy, treatment is generally instituted in order to minimize the symptoms and optimize the efficiency of the failing heart. Medication remains the mainstay of treatment, although there are no specific treatments for dilated cardiomyopathy other than those used in heart failure cases in general. Transplant surgery is one option. Indeed, dilated cardiomyopathy has been indicated as the most common cause for cardiac transplantation in the U.S.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

Treatment with pharmacological agents represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis).

Similarly, inotropic agent therapy (i.e., a drug that improves cardiac output by increasing the force of myocardial muscle contraction) may also be indicated if the diuretics do not result in adequate relief. The inotropic agent most commonly used by ambulatory patients is digitalis. However, it is associated with a panoply of adverse reactions, including gastrointestinal problems and central nervous system dysfunction.

Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities. The prognosis for patients with DCM is variable, and depends upon the degree of ventricular dysfunction, with the majority of deaths occurring within five years of diagnosis.

I. The Present Invention

The inventors have shown previously that MEF2 is activated by MAP kinase phosphorylation of three conserved sites in its carboxy-terminal activation domain (see, Katoh et al 1998). CaMK signaling also activates MEF2 by phosphorylating the class II HDACs, which are expressed at high levels in the adult heart where they can repress MEF2 activity. Upon phosphorylation, these HDACs bind to 14-3-3, and dissociate from MEF2, with resulting translocation to the nucleus and activation of MEF2-dependent transcription. Mutants of class II HDACs that cannot be phosphorylated cannot detach from MEF2 and irreversibly block expression of MEF2 target genes.

It has also been shown that an adenovirus encoding a non-phosphorylatable mutant of HDAC 5 is capable of preventing cardiomyocyte hypertrophy in vitro in response to diverse signaling pathways (see, Lu et al., 2000). These findings suggest that phosphorylation of these conserved sites in class II HDACs is an essential step for initiating cardiac hypertrophy. Based on these finding, one might expect that inhibition of HDAC activity by TSA would result in the induction of cardiac hypertrophy because of derepression of hypertrophic responsive genes. On the contrary, the present inventors found instead that TSA actually prevents cardiac hypertrophy. These unexpected findings suggest that at least some HDACs are required for hypertrophy and that inhibition of HDAC catalytic activity can prevent activation of hypertrophic genes.

How can these apparently conflicting results be explained? One model argues that class I and II HDACs may control different sets of genes in cardiomyocytes. According to this model, class II HDACs interact with and repress the activity of transcription factors, such as MEF2, that are required for hypertrophy, which would explain why non-phosphorylatable mutants of class II HDACs block hypertrophy. In contrast, it is proposed that class I HDACs, HDAC 1 and HDAC 3 in particular, suppress the expression of anti-hypertrophic genes. Thus, exposure of cardiomyocytes to TSA would result in derepression of these anti-hypertrophic genes and a blockade of hypertrophy. This model also predicts that the activity of such anti-hypertrophic genes would be dominant over the activity of class II HDACs, since they too are repressed by TSA, which would be expected to derepress the hypertrophic program.

In any event, and regardless of the precise molecular basis, the present invention shows that, surprisingly, HDAC inhibitors are beneficial in the treatment of cardiac hypertrophy and heart failure.

II. Histone Deacetylase

Nucleosomes, the primary scaffold of chromatin folding, are dynamic macromolecular structures, influencing chromatin solution conformations (Workman and Kingston, 1998). The nucleosome core is made up of histone proteins, H2A, HB, H3 and H4. Histone acetylation causes nucleosomes and nucleosomal arrangements to behave with altered biophysical properties. The balance between activities of histone acetyl transferases (HAT) and deacetylases (HDAC) determines the level of histone acetylation. Acetylated histones cause relaxation of chromatin and activation of gene transcription, whereas deacetylated chromatin generally is transcriptionally inactive.

Eleven different HDACs have been cloned from vertebrate organisms. The first three human HDACs identified were HDAC 1, HDAC 2 and HDAC 3 (termed class I human HDACs), and HDAC 8 (Van den Wyngaert et al., 2000) has been added to this list. Recently class II human HDACs, HDAC 4, HDAC 5, HDAC 6, HDAC 7, HDAC 9, and HDAC 10 (Kao et al., 2000) have been cloned and identified (Grozinger et al., 1999; Zhou et al. 2001; Tong et al., 2002). Additionally, HDAC 11 has been identified but not yet classified as either class I or class II (Gao et al., 2002). All share homology in the catalytic region. HDACs 4, 5, 7, 9 and 10 however, have a unique amino-terminal extension not found in other HDACs. This amino-terminal region contains the MEF2-binding domain. HDACs 4, 5 and 7 have been shown to be involved in the regulation of cardiac gene expression and in particular embodiments, repressing MEF2 transcriptional activity. The exact mechanism in which class II HDAC's repress MEF2 activity is not completely understood. One possibility is that HDAC binding to MEF2 inhibits MEF2 transcriptional activity, either competitively or by destabilizing the native, transcriptionally active MEF2 conformation. It also is possible that class II HDAC's require dimerization with MEF2 to localize or position HDAC in a proximity to histones for deacetylation to proceed.

III. Deacetylase Inhibitors

A variety of inhibitors for histone deacetylase have been identified. The proposed uses range widely, but primarily focus on cancer therapy. Saunders et al. (1999); Jung et al. (1997); Jung et al. (1999); Vigushin et al. (1999); Kim et al. (1999); Kitazomo et al. (2001); Vigusin et al. (2001); Hoffmann et al. (2001); Kramer et al. (2001); Massa et al. (2001); Komatsu et al. (2001); Han et al. (2001). Such therapy is the subject of an NIH sponsored Phase I clinical trial for solid tumors and non-Hodgkin's lymphoma. HDAC's also increase transcription of transgenes, thus constituting a possible adjunct to gene therapy. Yamano et al. (2000); Su et al. (2000).

HDACs can be inhibited through a variety of different mechanisms—proteins, peptides, and nucleic acids (including antisense and RNAi molecules). Methods are widely known to those of skill in the art for the cloning, transfer and expression of genetic constructs, which include viral and non-viral vectors, and liposomes. Viral vectors include adenovirus, adeno-associated virus, retrovirus, vaccina virus and herpesvirus.

Also contemplated are small molecule inhibitors. Perhaps the most widely known small molecule inhibitor of HDAC function is Trichostatin A, a hydroxamic acid. It has been shown to induce hyperacetylation and cause reversion of ras transformed cells to normal morphology (Taunton et al., 1996) and induces immunsuppression in a mouse model (Takahashi et al., 1996). It is commercially available from BIOMOL Research Labs, Inc., Plymouth Meeting, Pa.

The following references, incorporated herein by reference, all describe HDAC inhibitors that may find use in the present invention: AU 9,013,101; AU 9,013,201; AU 9,013,401; AU 6,794,700; EP 1,233,958; EP 1,208,086; EP 1,174,438; EP 1,173,562; EP 1,170,008; EP 1,123,111; JP 2001/348340; U.S. 2002/103192; U.S. 2002/65282; U.S. 2002/61860; WO 02/51842; WO 02/50285; WO 02/46144; WO 02/46129; WO 02/30879; WO 02/26703; WO 02/26696; WO 01/70675; WO 01/42437;WO 01/38322; WO 01/18045; WO 01/14581; Furumai et al. (2002); Hinnebusch et al. (2002); Mai et al. (2002); Vigushin et al. (2002); Gottlicher et al. (2001); Jung (2001); Komatsu et al. (2001); Su et al. (2000).

Examples of some specific HDAC inhibitors are shown in Table 1.

TABLE 1

| Inhibitor | Compound Type | Chemical Composition | Organism |
|---|---|---|---|
| Trapoxin B | porphyrin derivative | $C_{33}H_{30}N_4O_6$ | H. ambiens |
| MS-27-275 | benzamide derivative | $C_{21}H_{20}N_4O3$ | |
| Scriptaid | hydroxamic acid | $C_{18}H_{12}N_2O_4$ | |
| FR901228 | cyclopeptide | $C_{24}H_{36}N_4O_6S_2$ | C. violaceum (#968) |
| Depudecin | fungal metabolite | $C_{11}H_{16}O_4$ | A. brassiciola |
| Oxamflatin | aromatic sulfonamide | $C_{18}H_{14}N_2O_4S_1$ | |
| Pyroxamide (suberoyl-3-aminopyridineamide hydroxyamic acid) | hydroxamic acid | $C_{13}H_{20}N_3O_3$ | |
| 2-amino-8-oxo-9,10-epoxy-decanoyl (AEO) | ketone | $C_{10}H_{17}NO_3$ | |
| 3-(4-aroyl-1 H-pyrrol-2-yl)-N-hydroxy-2-propenamide | propenamide | $C_{14}H_{12}N_2O_3$ | |
| Suberoylanilide hydroxamic acid | hydroxamic acid | $C_{14}H_{20}N_2O_3$ | |
| m-Carboxycinnamic acid bis-hydroxamide | hydroxamic acid | $C_{10}H_{10}N_2O_4$ | |
| Apicidin[1] | cyclopeptide | $C_{29}H_{38}N_5O_6$ | Fusarium spp. |
| CHAP1 (trichostatin A + trapoxin B) | hydroxamic/porphryin derivatives | | |

[1] cyclo(N-O-methyl-L-tryptophanyl-L-isoleucinyl-D-pipecolinyl-L-2-amino-8-oxodecanoyl)

IV. Methods of Treating Cardiac Hypertrophy

A. Therapeutic Regimens

In one embodiment of the present invention, methods for the treatment of cardiac hypertrophy utilizing HDAC inhibitors are provided. For the purposes of the present application, treatment comprises reducing one or more of the symptoms of cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle. In addition, use of HDAC inhibitors may prevent cardiac hypertrophy and its associated symptoms from arising.

Treatment regimens would vary depending on the clinical situation. However, long term maintenance would appear to be appropriate in most circumstances. It also may be desirable treat hypertrophy with HDAC inhibitors intermittently, such as within brief window during disease progression. At present, testing indicates that the optimal dosage for an HDAC inhibitor will be the maximal dose before significant toxicity occurs.

B. Combined Therapy

In another embodiment, it is envisioned to use an HDAC inhibition in combination with other therapeutic modalities. Thus, in addition to the therapies described above, one may also provide to the patient more "standard" pharmaceutical cardiac therapies. Examples of standard therapies include, without limitation, so-called "beta blockers," antihypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the HDAC inhibitor therapy may precede or follow administration of the other agent by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an HDAC inhibitor, or the other agent will be desired. In this regard, various combinations may be employed. By way of illustration, where the HDAC inhibitor is "A" and the other agent is "B", the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated.

C. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifingal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifingal agents, for example, parabens, chlorobutanol, phenol, sorbic acid, thimerosal, and the like; In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Screening Methods

The present invention further comprises methods for identifying inhibitors of HDACs that are useful in the prevention or reversal of cardiac hypertrophy. These assays may comprise random screening of large libraries of candidate substances; alternatively, the assays may be used to focus on particular classes of compounds selected with an eye towards structural attributes that are believed to make them more likely to inhibit the function of HDACs.

To identify an HDAC inhibitor, one generally will determine the function of an HDAC in the presence and absence of the candidate substance. For example, a method generally comprises:

(a) providing a candidate modulator;

(b) admixing the candidate modulator with an HDAC;

(c) measuring HDAC activity; and (d) comparing the activity in step (c) with the activity in the absence of the candidate modulator, wherein a difference between the measured activities indicates that the candidate modulator is, indeed, a modulator of the compound, cell or animal.

Assays also may be conducted in isolated cells or in organisms. Typically, HDAC activity is measured by providing a histone with a labeled acetyl group and measuring release of the label from the histone molecule.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit HDAC activity. The candidate substance may be a protein or fragment thereof, a small molecule, or even a nucleic acid. It may prove to be the case that the most useful pharmacological compounds will be compounds that are structurally related to known HDAC inhibitors, listed elsewhere in this document. Using lead compounds to help develop improved compounds is known as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a finctional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecular libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

2. In vitro Assays

A quick, inexpensive and easy assay to run is an in vitro assay. Such assays generally use isolated molecules, can be run quickly and in large numbers, thereby increasing the amount of information obtainable in a short period of time.

A variety of vessels may be used to run the assays, including test tubes, plates, dishes and other surfaces such as dipsticks or beads.

A technique for high throughput screening of compounds is described in WO 84/03564. Large numbers of small peptide test compounds are synthesized on a solid substrate, such as plastic pins or some other surface. Such peptides could be rapidly screening for their ability to bind and inhibit HDACs.

3. In cyto Assays

The present invention also contemplates the screening of compounds for their ability to modulate HDACs in cells. Various cell lines can be utilized for such screening assays, including cells specifically engineered for this purpose.

4. In vivo Assays

In vivo assays involve the use of various animal models of heart disease, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to. Also, measuring toxicity and dose response can be performed in animals in a more meaningful fashion than in in vitro or in cyto assays.

VI. Definitions

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rates and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "agonist" refers to molecules or compounds which mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. Agonists may include proteins, nucleic acids, carbohydrates, or any other molecules that interact with a molecule, receptor, and/or pathway of interest.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the terms "antagonist" and "inhibitor" refer to molecules or compounds which inhibit the action of a cellular factor that may be involved in cardiac hypertrophy. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Alternatively, antagonists may prevent the function of the agonist. In contrast to the agonists, antagonistic compounds do not result in pathologic and/or biochemical changes within the cell such that the cell reacts to the presence of the antagonist in the same manner as if the cellular factor was present. Antagonists and inhibitors may include proteins, nucleic acids, carbohydrates, or any other molecules which bind or interact with a receptor, molecule, and/or pathway of interest.

As used herein, the term "modulate" refers to a change or an alteration in the biological activity. Modulation may be an increase or a decrease in protein activity, a change in binding characteristics, or any other change in the biological, finctional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adreno-receptors (i.e., receptors of the adrenergic system that respond to catecholamines, especially norepinephrine). Some β-adrenergic receptor antagonists exhibit a degree of specificity for one receptor sybtype (generally $β_1$); such antagonists are termed "$β_1$-specific adrenergic receptor antagonists" and "$β_2$-specific adrenergic receptor antagonists." The term β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the rennin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quiapril and ramipril. The use of derivatives of known ACE inhibitors is encompassed by the methods of the present invention. Indeed any compound, which functionally behaves as an ACE inhibitor, is encompassed by the methods of the present invention.

As used herein, the term "genotypes" refers to the actual genetic make-up of an organism, while "phenotype" refers to physical traits displayed by an individual. In addition, the "phenotype" is the result of selective expression of the genome (i.e., it is an expression of the cell history and its response to the extracellular environment). Indeed, the human genome contains an estimated 30,000–35,000 genes. In each cell type, only a small (ie., 10–15%) fraction of these genes are expressed.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. Ventricular myocytes from one-day-old rats were plated at low density in MEM with 5% calf serum, and studied in serum-free MEM. Cultures were treated with PE (#P6126, Sigma-Aldrich Corp., St. Louis, Mo.), IL-1 (#501-RL, R&D Systems, Minneapolis, Minn.), TSA (#GR-309, BIOMOL Research Laboratories, Inc., Plymouth Meeting, Pa.) or their vehicles (ascorbic acid for PE; bovine serum albumin for IL-1; dimethyl sulfoxide for TSA).

Detection of acetylated lysine residues. Total cell extract was subjected to Western blot analysis using antibodies from Cell Signaling Technology (Beverly, Mass.) (acetylated lysine antibody: #9441, acetylated histone H3 antibody at Lysine 9: #9671, acetylated histone H3 antibody at Lysine 23: #9674, histone H3 antibody: #9712). Nuclear localization of acetylated histone H3 was examined by inununostaining using the same antibodies.

Quantification of myocyte hypertrophy and myocyte-specific mRNA expression. Growth of cultured myocytes was quantified by content of radiolabeled protein after continuous incubation with $^{14}$C-phenylalanine. For evaluation of the myocyte gene program, total RNA was extracted from cells with TRIZol (GIBCO, Carlsbad, Calif.) and used in RNase protection assay with probes for SERCA, α-/β-MyHC, ANP, BNP, and cardiac α-actin. All samples also included glyceraldehyde phosphate dehydrogenase (GAPDH) as an internal control for RNA loading.

Transfection. Myocytes were transfected using calcium-phosphate co-precipitation with cytomegalovirus promoter driven Flag-tagged expression vectors for HDACs 1, 4, 5 and reporter plasmids carrying the rat promoters for SERCA (3500 bp), αMyHC (2900 bp), or βMyHC (3300 bp) driving expression 7 of the chroramphenicol acetyltransferase (CAT) gene. Reporter expression was evaluated after 48 hours as described previously with corection for transfection efficiency with SEAP (BD Biosciences Clontech, Palo Alto, Calif.). Over-expression of HDACs was confirmed by Western blot analyses using anti-Flag M2 antibody (Sigma-Aldrich Corp. St. Louis, Mo.).

Results

TSA increases protein acetylation in cardiac myocytes. Initial experiments were directed at confirming that TSA was able to inhibit HDAC activity in cardiac myocytes, reasoning that this should result in an overall increase in protein acetylation. The degree of acetylation was determined using antibodies specific for acetylated lysine residues. Inventors showed by both Western blot and cellular immunofluoresence analyses that exposure to TSA for 24 hours effectively increased acetylated lysine residues in a number of proteins and specifically those in Histone H3.

Figure 1B:
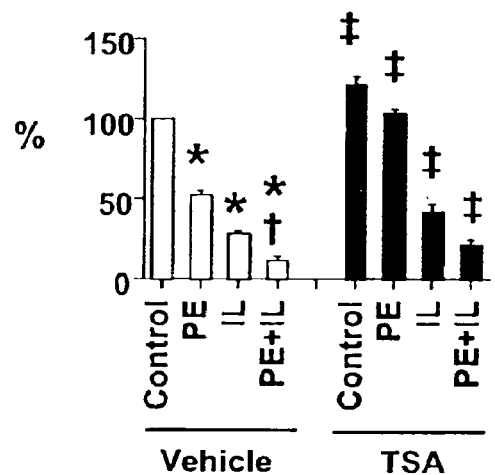
Figure 1C:
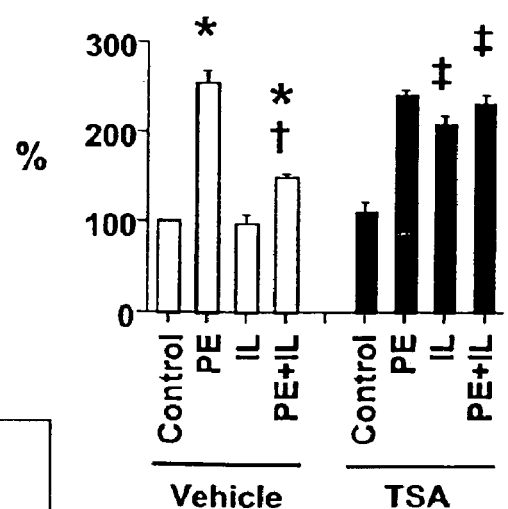

TSA enhances agonist-induced growth, but reverses hypertrophy associated gene repression. Although TSA by itself had no effect on myocyte growth, inventors found that it enhanced the individual hypertrophic responses to both PE and IL-1. Both hypertrophic stimuli down-regulated SERCA (FIG. 1A) and αMyHC (FIG. 1B) expression and the combined exposure to both agonists resulted in further repression. In contrast, TSA increased the basal expression of both SERCA2a and αMyHC mRNAs. TSA pre-treatment also resulted in a substantial reversal in the repression of SERCA expression by both hypertrophic stimuli. Notably, although TSA resulted in a nearly complete reversal of the PE effect on αMyHC expression, this effect was less prominent in the case of IL-1 treated (or co-treated) cells. Inventors previously showed that co-treatment of cardiac myocytes with both PE and IL-1 suppressed the usual PE induction of αMyHC expression by nearly 50%. It is intriguing that although TSA had no effects on either the basal expression or PE-induction of this gene, it increased αMyHC expression in the presence of IL-1 alone and reversed the IL-1 effect in PE/IL-1 co-treated cells. A similar reversal was also seen with the sACT gene (Wang and Long, unpublished data). Notably, TSA did not affect gene expression of cardiac α-actin, ANP, or BNP under any hypertrophic treatment condition (data not shown).

Figure 2A:
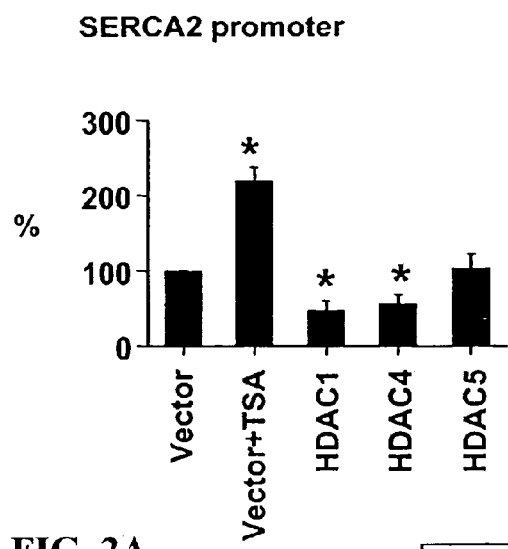
FIGS. 2A–D. Over-expression of HDACs repress muscle-specific promoters. Cultured myocytes were transfected for 72 hrs. with expression vectors (2 μg per ~3×105 cells) for Flag-tagged HDAC1, 4, 5 (or its backbone vector) and CAT reporter (5 μg) constructs for SERCA (FIG. 2A), αMyHC (FIG. 2B), βMyHC (FIGS. 2C and 2D) genes, plus SV40-driven secreted alkaline phosphatase (SEAP 1 μg, Clontech). TSA was used at 30 nmol/L, and added just after the transfection. PE 22 (20 μmol/L) was added 24 hrs. later and CAT assays performed after an additional 48 hours. Mean data are from n=3 different cultures, and are presented as % of pCMV after normalization to SEAP activity in the media. Over-expression of HDAC was confirmed by Western blot for Flag.
Figure 2B:
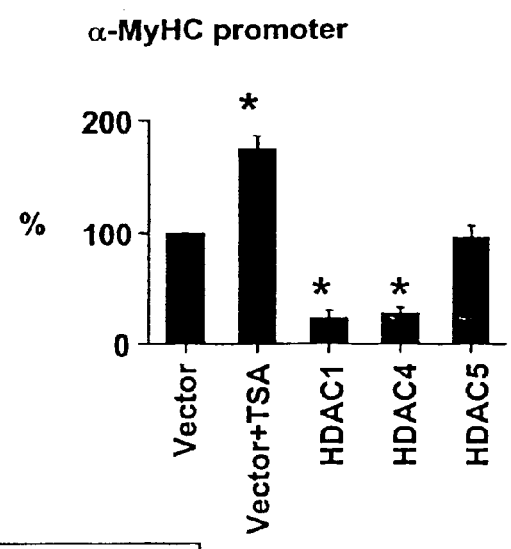
Figure 2C:
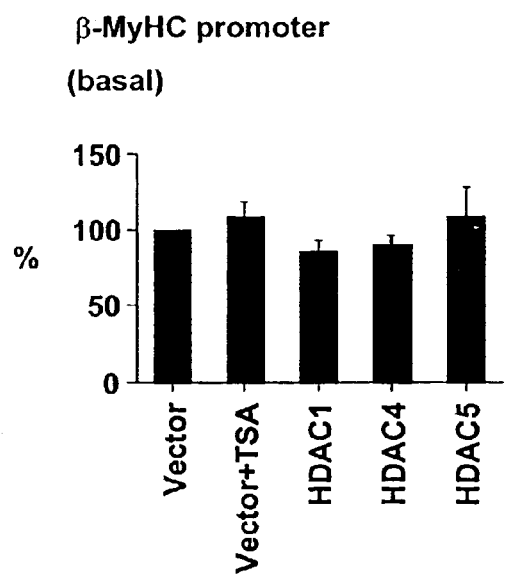
Figure 2D:
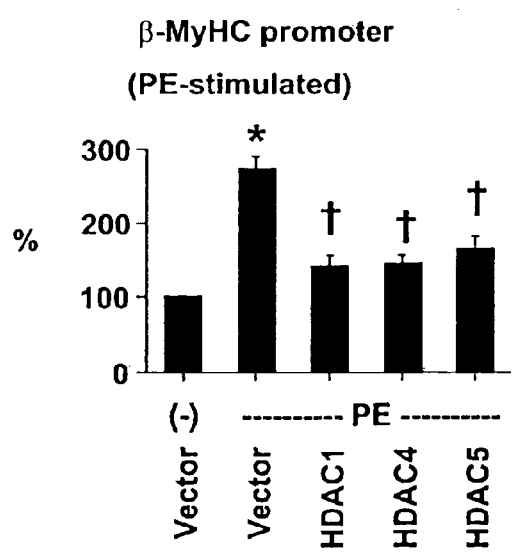

Over-expression of HDAC repressed promoter activities of myocyte-specific genes. In agreement with the studies of mRNA expression for these target genes, TSA also increased the basal promoter activities of both SERCA2 (FIG. 2A) and αMyHC (FIG. 2B) genes but not that of βMyHC (FIG. 2C). Further, co-transfection of these constructs with expression vectors for HDACs1 or 4 also decreased promoter activities for both SERCA (FIG. 2A) and αMyHC (FIG. 2D) genes. In contrast, however, HDAC5 failed to inhibit the promoter activities of either gene despite levels of expression similar to that of the other isoforms (data not shown). Notably, all three HDAC constructs were able to attenuate the PE-induced increase in αMyHC promoter activity (FIG. 2D).

Example 2

Materials and Methods

Cardiomyocyte isolation. Hearts were harvested from 15-day timed-pregnant female Sprague-Dawley rats (Harlan, Houston, Tex.). After mincing in phosphate-buffered saline, cardiomyocytes were isolated from successive digestion fractions of 0.1% (w/v) Pancreatin (Sigma, St. Louis, Mo.) solution. Fractions were collected; resuspended in plating medium, pooled; and then plated for 2 hours to separate fibroblasts from cardiomyocyte population. Suspended cells were recollected and plated in 6-well dishes at $1 \times 10^6$ cells/well for transfection and immunofluorescence experiments, and $2 \times 10^6$ cells in 10 cm dishes for RNA analysis.

Transcription assay. Twenty-four hours after plating, cells were transfected with total of 1 μg/ml for 5 hrs using Lipofectamine Plus reagent (Invitrogen, Carlsbad, Calif.). Transfected cells were incubated 24 hrs then treated for an additional 24 hrs. Cells were lysed and their lysates assayed with the Luciferase Assay System (Promega, Madison, Wis.) for luminescence using Lucysoft 2 luminometer (Rosys Anthos, New Castle, Del.).

Chemilumenescence. Neonatal cardiomyocytes were seeded onto 96-well plates and treated for 72 hrs. The cells were washed twice in 1×PBS, fixed in 4% paraformaldehyde/1×PBS, and permeabilized with 0.1% Triton-X100. After blocking, the cells were incubated 1 hr. with 10 μg/ml monoclonal anti-ANF antibody (Biodesign). The wells were washed twice with 1% BSA/1×PBS and then incubated for 1 hr. with goat anti-mouse IgG-Fc-HRP (Jackson Labs, location) at 1:1000 in 1×PBS/1% BSA. Cells were washed twice with 1% BSA/1×PBS, twice with 1×PBS, then blotted dry. Luminol (Pierce, Rockford, Ill.) was added and the chemiluminescence was detected in a Fusion Plate Reader (Perkin Elmer/Packard).

Dot Blot analysis. Total RNA was isolated from cardiomyocytes that were either untreated, treated with phenylephrine, treated with TSA, or co-treated with phenylephrine and TSA. One microgram of RNA was blotted onto Nitrocellulose (Bio-Rad, Hercules, Calif.) and hybridized at 50° C. for 14 hrs with end-labeled oligos. (ANF, 5'-aatgtgaccaagctgcgtgacacaccacaagggcttaggatcttttgcgat ctgctcaag-3', SEQ ID NO 1; αSK actin5'-tggagcaaa acagaatggctggctttaatgcttcaagttttccatttcctttccacaggg-3', SEQ ID NO2; αMyHC, 5'cgaacgtttatgtttattgtggattggc-cacagcgagggt ctgctggagagg-3', SEQ ID NO 3; βMyHC5'-gctttattctgcttccacctaaagggctgttgcaaaggctccaggtctgagggcttc-3', SEQ ID NO 4; GAPDH5'-ggaacatgtagaccatgtag ttgaggtcaatgaag-3', SEQ ID NO 5). The blots were washed twice in 2×SSC/0.5% SDS solution and exposed to film (Kodak, Rochester, N.Y.) or phosphoimager (Amersham Bioscience, Sunnyvale, Calif.). The intensity of the hybridization of the probes was measured using ImageQuant© (Amersham Bioscience, Sunnyvale, Calif.).

Immunostaining. Glass coverslips were coated with laminin (Invitrogen, Carlsbad, Calif.) by solublizing laminin in 1×PBS (40 μg/ml), by dipping the coverslips in the solution and by allowing them to air-dry. Cells were treated for 24 hrs, washed, fixed 10 min. with 3.7% formaldehyde, washed with 1×PBS and permeabolized with 1×PBS containing 3% BSA and 0.1% NP-40 (Sigma, St. Louis, Mo.). Primary Antibodies were in 1×PBS containing 3% BSA and 0.1% NP-40 for 30 min, then washed three times in 1×PBS. The secondary FITC or TRITC antibodies (Vector Laboratories, Inc., Burlingame, Calif.) were incubated (1:200) in same buffer solution as the primary antibodies, then washed in 1×PBS, covered and subsequently visualized. Images were captured using a digital camera (Hamamatsu Photonics, Hamamatsu City, Japan).

Protein synthesis. Cardiomyocytes were incubated with (1.0 μCi/ml; 172 Ci/mmol sp. activity) tritiated-leucine (ICN Biochemicals, Inc., Irvine, Calif.) in treated RPMI media (Invitrogen, Carlsbad, Calif.). After 6 hrs incubation, the cells were washed twice with 1×PBS, then incubated in 10% TCA on ice for 30 min. Afterwards, the cells were washed twice with 5% TCA, once with water, and then lysed in 0.25 NaOH. Lysates were measured in one-sixth volume of scintillation fluid by a scintillation counter (Beckman, Fullerton, Calif.).

S6 Ribosomal protocol. After blocking, cells were incubated in 1% BSA/1×PBS containing 50 μg/ml anti-S6 protein (Cell Signaling, location) for 1 hr. After washing, the cells were incubated with IgG-HRP (Jackson Labs, location) at a 1:400 dilution. The cells were then washed twice in 1% BSA/1×PBS, in 1×PBS, then blotted dry. Luminol (Pierce, Rockford, Ill.) was added and the chemiluminescence was detected in a Fusion reader (Perkin-Elmer/Packard).

Gene chip and analysis. RNA was isolated using Trizol (Invitrogen, Carlsbad, Calif.) from untreated, phenylephrine-treated, TSA-treated, and phenylephine/TSA co-treated rat neonatal cardiomyocytes. The RNAs were prepared and hybridized on U34A chips (Affymetrix, Inc., Santa Clara, Calif.) according to Affymetrix protocols. The intensity of hybridization was detected by and changes in gene expression were determined and analyzed by Micro Array Suite 5.0 (Affymetrix, Inc., Santa Clara, Calif.).

Results

Figure 3B:
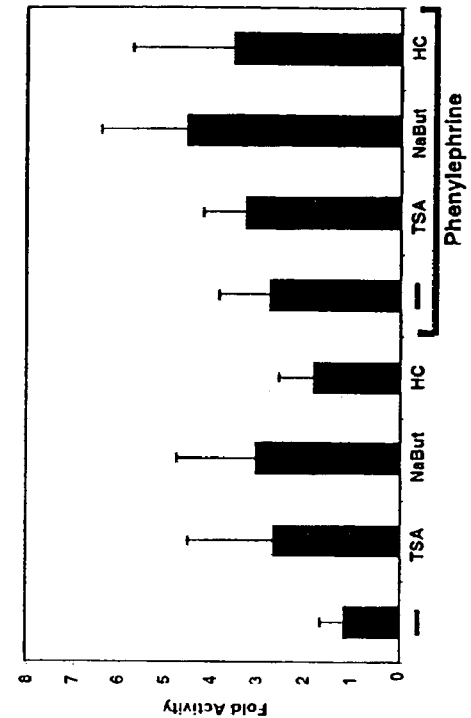
FIGS. 3A–D. HDAC inhibitors block the activation of ANF reporter by phenylphrine without cytotoxicity. Neonatal rat cardiomyocytes were co-transfected with a total of 1 μg of the mouse 3 kb ANF promoter fragment and CMV-Lac Z plasmids.
Figure 3D:
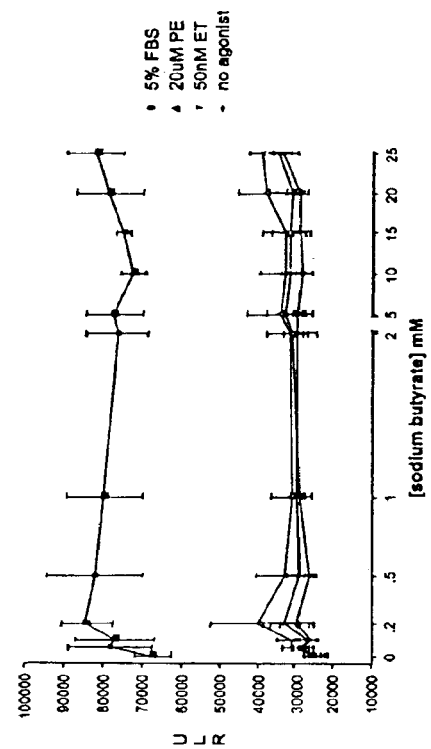
Figure 3A:
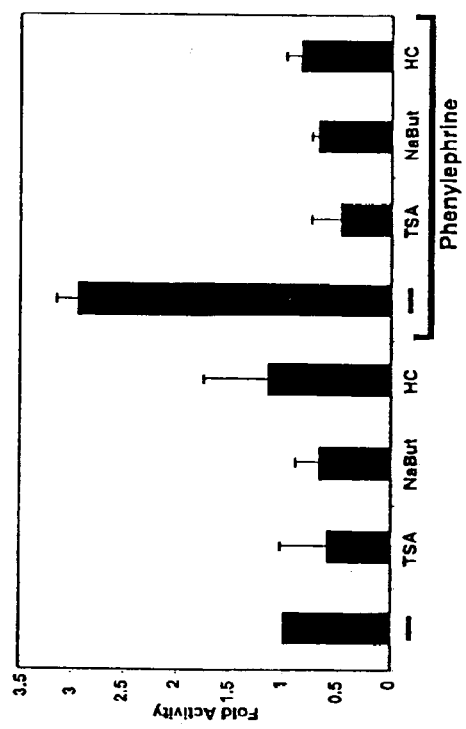

Because histone deacetylases (HDACs) regulate gene expression, the inventors analyzed whether HDAC inhibition would alter the expression of genes associated with cardiac hypertrophy. Atrial natriuretic factor (ANF) is one such gene, and its expression increases in presence of the hypertrophic agonists. In order to determine whether HDAC inhibition affects ANF gene activation, transfection experiments were performed with the ANF promoter and transfected cardiomyocytes were treated with phenylephrine and several HDAC inhibitors. Treatment of cardiomyocytes with trichostatin (TSA), sodium butyrate (NaBut) or HC-toxin (HC) did not activate the ANF promoter. The HDAC inhibitors, however, did block the promoter's activation by phenylephrine treatment completely (FIG. 3A). This effect was specific, because cardiomyocytes treated either with each HDAC inhibitor alone or together with phenylephrine increased the transcriptional activity of the CMV-Lac Z reporter (FIG. 3B), indicating that the action of these pharmacological agents was specific to the transcriptional control of ANF and not from general transcriptional inhibition.

Figure 3C:
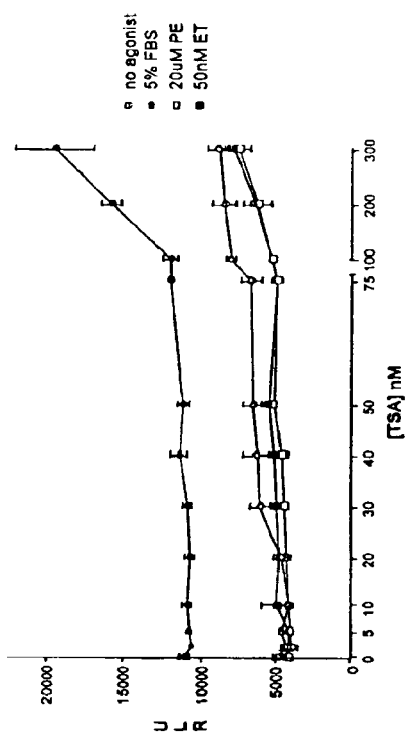

Inventors then examined whether increasing doses of TSA and sodium butyrate were cytotoxic to cultured cardiomyocytes. To determine cell mortality, the release of adenylate kinase from cardiomyocytes into the culture medium was assayed. This assay is a known measurement for the integrity of the cell membrane: membranes become permeable in dying cells causing the cells release adenylate kinase. Increasing doses of TSA (up to 100 nM) and sodium butyrate (up to 25 nM) did little to increase adenylate kinase in the culture medium, indicating an absence of increased cell death by TSA and sodium butyrate (FIGS. 3C & 3D). In the single time-point experiments, 85 nM TSA or 5 mM sodium butyrate were used, so these results indicate that inactivation of ANF transcription is a direct effect of HDAC inhibition and not an indirect consequence of cytotoxicity by the HDAC inhibitors.

Figure 4A:
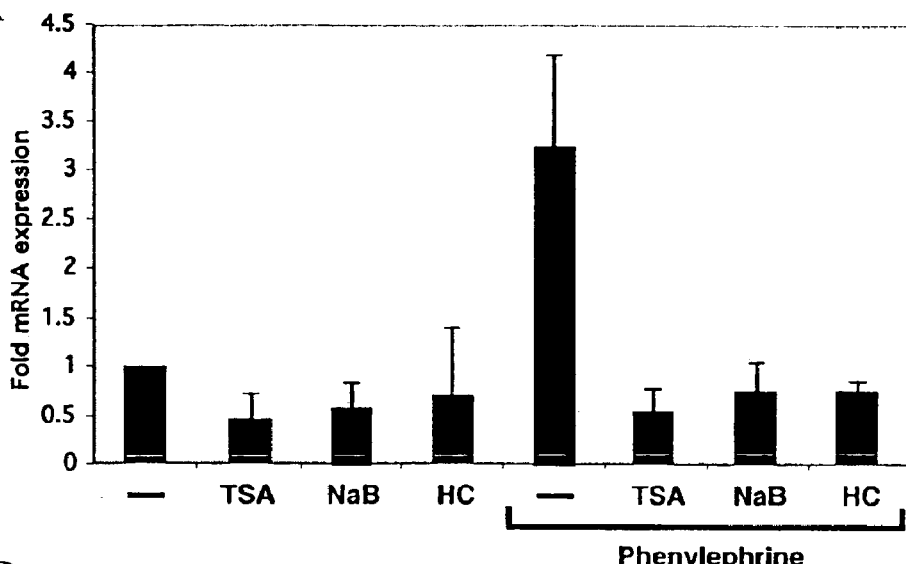
FIGS. 4A–C. HDAC inhibitors prevent endogenous ANF expression normally induced by hypertrophic agonists.

To determine whether endogenous gene expression paralleled the transfection results, the inventors looked at endogenous RNA levels of ANF from cardiomyocytes under the various treatment conditions. RNA dot blot analysis of phenylephrine-treated cardiomyocytes showed an approximate three-fold increase in the expression of ANF in response to phenylephrine treatment; however, co-treatment of phenylephrine-treated cells with the different HDAC inhibitors (TSA, NaBut or HC-toxin) prevented the phenylephrine-induced ANF response (FIG. 4A), in agreement with the transfection results previously mentioned.

Figure 4B:
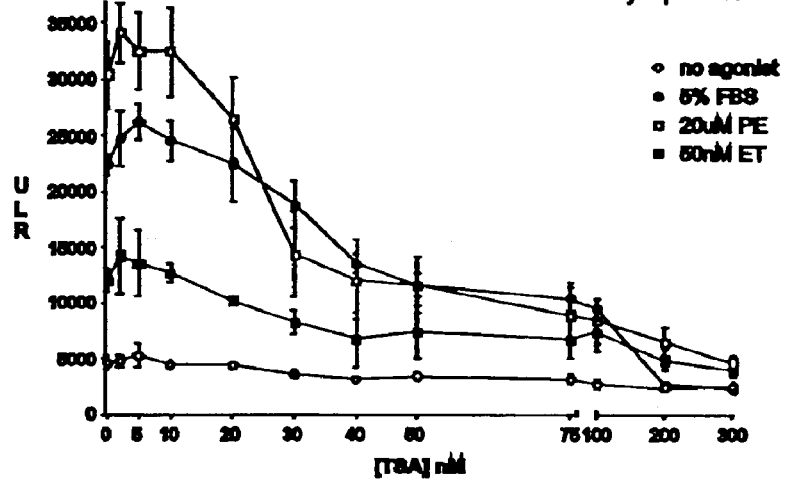
Figure 4C:
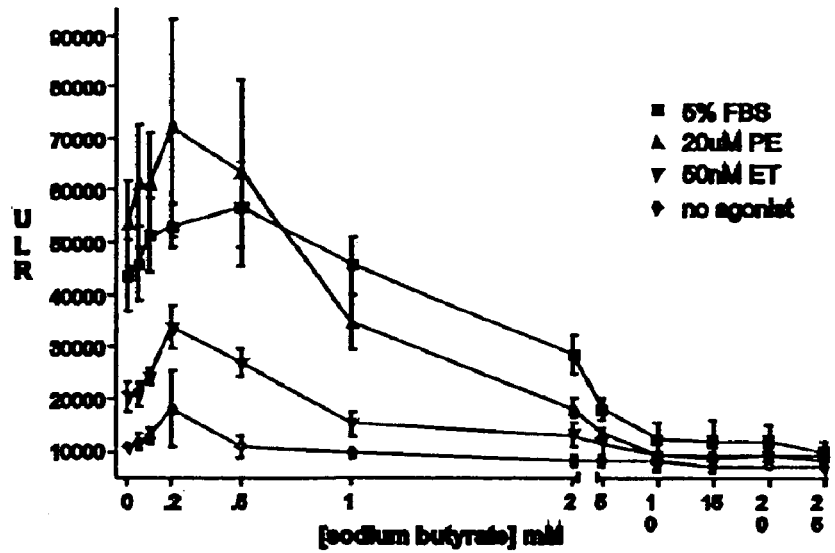

Prior data has shown that a low dose of TSA can induce the ANF expression by acetylation of the ANF locus and by inactivation of the transcription repressor, NRSE. To address whether there is a dose-dependent effect of HDAC inhibitors, inventors examined ANF expression after treating primary cardiomyocytes with increasing concentrations of TSA (FIG. 4B) and sodium butyrate (FIG. 4C) in the absence and presence of the hypertrophic stimulants serum (FBS), phenylephrine (PE) or endothelin-1 (ET-1). At very low doses (0.2 nM) of sodium butyrate (FIG. 4C), inventors observed a near two-fold increase in ANF expression. There was only a marginal increase increase with TSA (FIG. 4B). However, the HDAC inhibitors at all other concentrations did not induce ANF production, and with increasing concentrations, they countered the induction of ANF expression normally observed after treating cultured cardiomyocytes with the growth stimulants FBS, PE and ET-1 (FIGS. 4B and C). The minimal concentrations that inhibited the hypertrophic response of each growth stimulant were 40 nM TSA and 5 mM sodium butyrate, which mimicked the three-to-four-fold reduction of ANF in transcription observed in the transfection and dot blot experiments. These doses were well below the threshold of cytotoxicity.

Figure 5A:
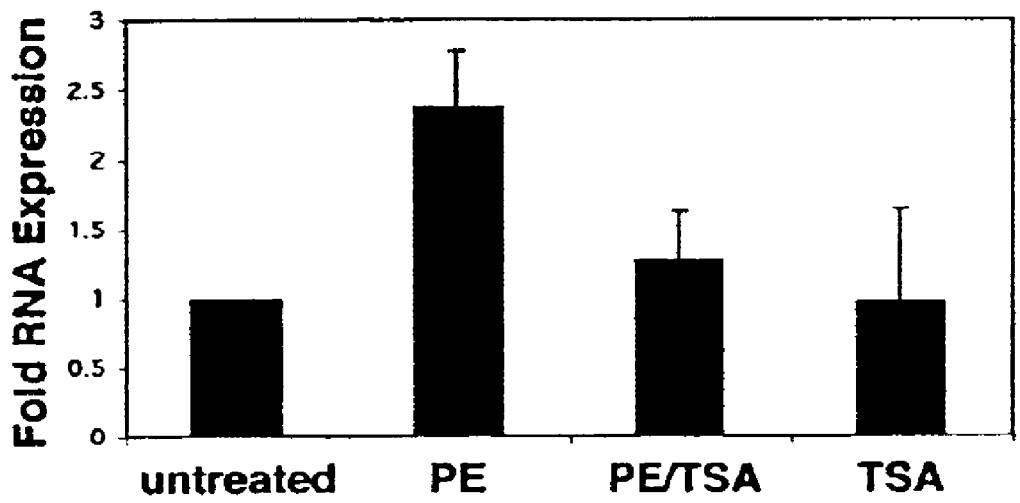
FIGS. 5A–B. Treatment of cardiomyocytes with HDAC inhibitors blocks the fetal gene program associated with cardiomyocyte hypertrophy.
Figure 5B:
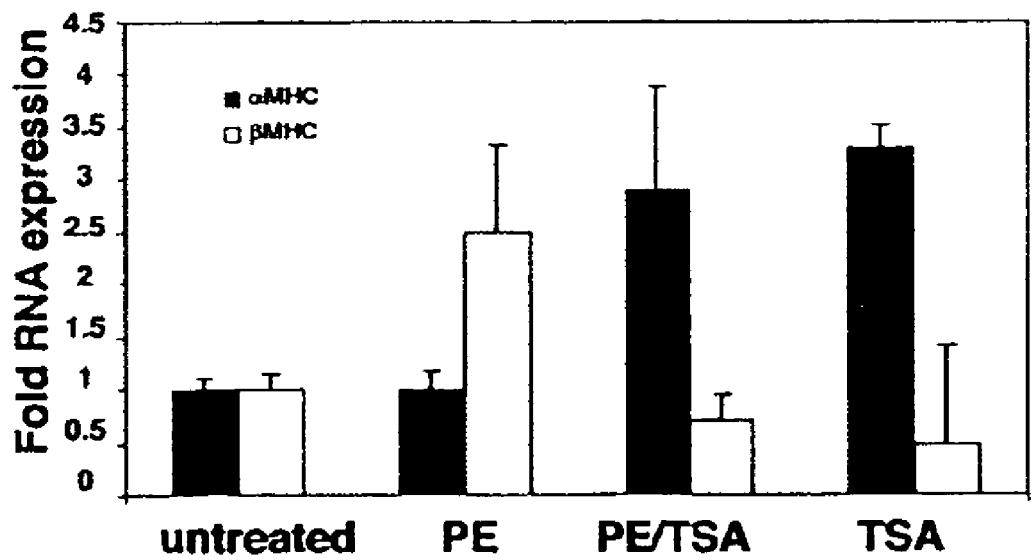

Cardiac hypertrophy is associated with the reprogramming of fetal genes in addition to ANF. The inventors wished to determine whether other members of the fetal gene cascade were affected by treatment of TSA. Quantitative analysis of the fold change of α-sk expression and βMyHC, in addition to ANF, showed that HDAC inhibition resulted in the suppression of other genes activated by the hypertrophic stimulant, phenylephrine (FIGS. 5A and B). Furthermore, in addition to down-regulating the fetal myosin chain isoform (βMyHC) isoform, TSA treatment of cardiac myocytes induced the expression of αMyHC, the adult myosin heavy chain isoform normally reduced in hypertrophic cardiomyocytes (FIG. 5B). These data taken together indicate that HDAC inhibition suppresses the transcriptional reprogramming of the gene cascade associated with cardiomyocyte hypertrophy.

Staining for ANF protein showed that cardiomyocytes treated with phenylephrine or serum induced a perinuclear accumulation of ANF protein compared to unstimulated cells (data not shown). Cardiomyocytes treated with TSA lacked accumulation of ANF protein and the addition of TSA to cardiomyocytes treated either with phenylephrine or with serum dramatically reduced ANF protein accumulation. Immunocytochemical staining for α-actinin showed that HDAC inhibition antagonized the reorganization of the sarcomere, another phenomenon associated with cardiomyocyte hypertrophy. Unstimulated cardiomyocytes maintained an amorphous shape with no apparent structural organization of the sarcomere (α-actinin). Hypertrophic agonists phenylephrine, serum, and ET-1 potently stimulated the organization of the sarcomere as part of a highly ordered cytoskeletal structure. Interestingly, TSA did affect cardiomyocyte morphology. Although TSA-treated cells did not change size, they tended to acquire a "starred" appearance by growing narrow extensions from the main body of the cell. However, they lacked organization of the sarcomere. The effect of TSA treatment was more dramatic in the presence of growth stimulants, because it affected the hypertrophic morphology normally induced by phenylephrine, serum or ET-1. TSA-treated cardiomyocytes lacked fully organized sarcomeres.

Figure 6:
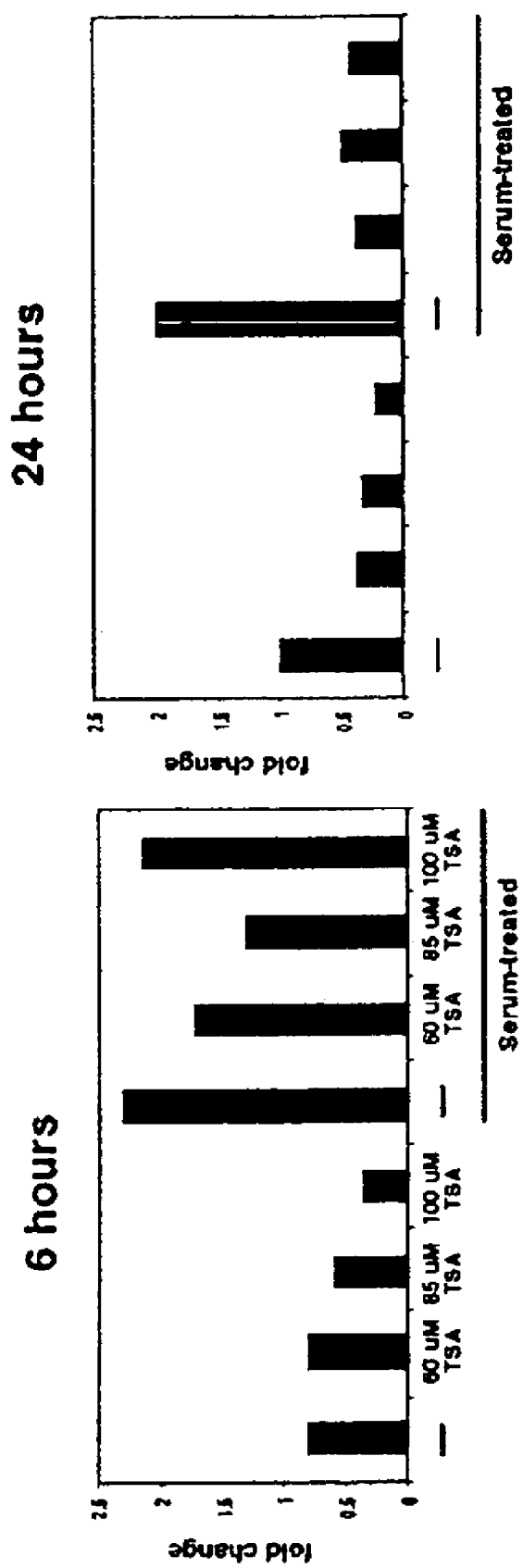

The inventors then determined whether TSA antagonized the increase in protein synthesis normally associated with the hypertrophic response by assaying for changes in protein synthesis and measuring the accumulation of the protein content of the ribosomal subunit, S6. Phenylephrine boosted protein synthesis in the cardiac myocytes by two-fold after 6 hours of stimulation; however, co-culturing phenylephrine with the HDAC inhibitors TSA and sodium butyrate had little effect on the stimulation of protein synthesis normally induced with phenylephrine (FIG. 6). Yet, by 24 hrs after co-treatment, HDAC inhibitors antagonized the protein synthesis normally induced by PE or serum in a dose-dependent manner (FIG. 6). This suggests that the prevention of the organization of the sarcomere by HDAC inhibition is an effect specific to transcription regulation.

Previous work has shown that TSA treatment of yeast results in a change in gene expression in only a subset of genes. If this is true for cardiomyocytes, then it is possible that a limited number of genes are responsible for the suppression of the hypertrophic phenotype. To identify these genes, inventors assayed the expression of approximately eight-thousand genes by gene chip array. Subsequent graphic analysis of the assays of the expression between the gene changes in the phenylephrine- and phenylephrine/TSA-treated cells revealed that the majority of genes clustered linearly. The majority of transcripts remained relatively unchanged (less than a three-fold change in gene expression) between the chip hybridized with RNA from phenylephrine-treated cells and the chip hybridized with RNA from phenylephrine/TSA-treated cells. This suggests that the relative number of genes responsible for the suppression of phenylephrine-induced cardiomyocyte growth by TSA treatment is low.

Figure 7A:
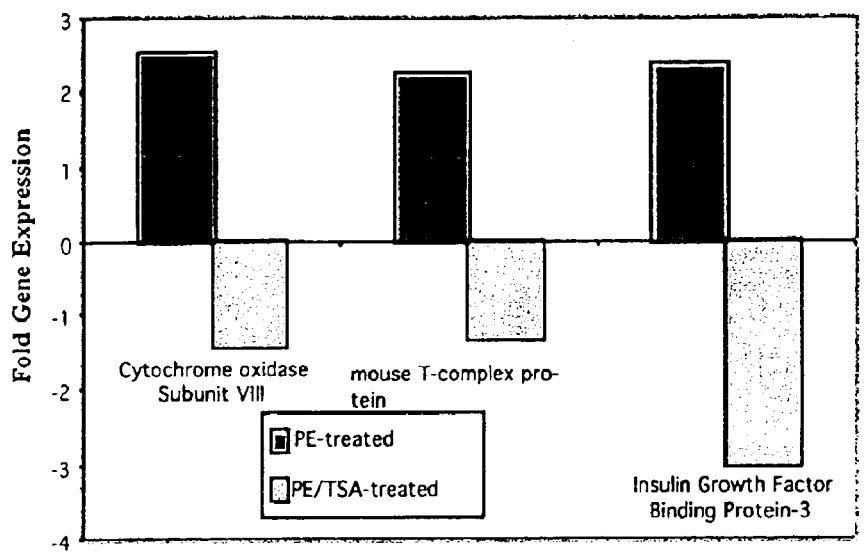
FIGS. 7A–B. TSA induces the activation of genes that are involved in cardiomyocyte differentiation.
Figure 7B:
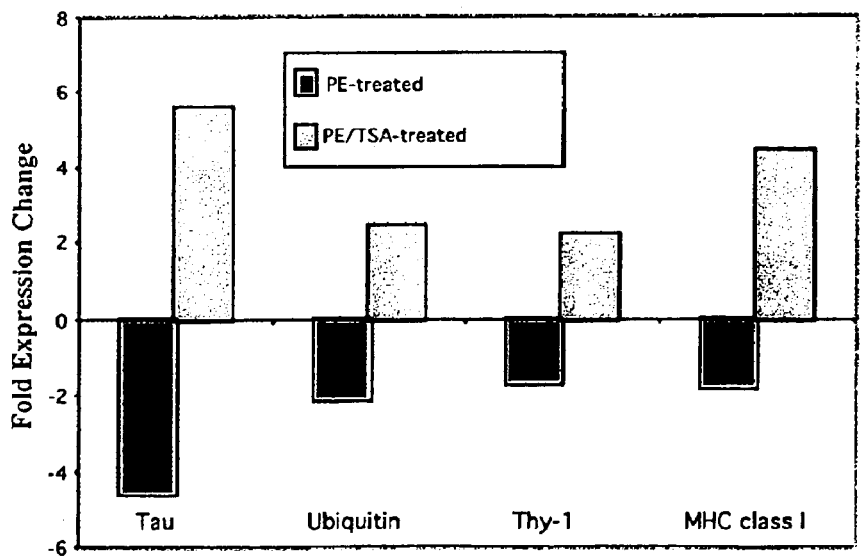

From the reduced number of genes whose expression levels were altered by phenylephrine, TSA or their combination, inventors identified seven genes that had a consistent two-or-more-fold difference between phenylephrine treatment and the TSA-treated groups: phenylephrine/TSA and TSA. Three genes were up-regulated by phenylephrine treatment and down-regulated by TSA: cytochrome oxidase subunit VIII, mouse T-complex protein and insulin growth factor binding protein-3 (FIG. 7A). Four genes down-regulated by phenylephrine and up-regulated by TSA were big Tau-microtubule-associated protein, ubiquitin carboxyl-terminal hydrolase, Thy-1 cell-surface glycoprotein and MyHC class I antigen (FIG. 7B). Northern analysis confirmed the expression results of the gene chip array (data not shown).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. References

The following references, to the extent that they provide exemplary procedural or other details supplementary to those set forth herein, are specifically incorporated herein by reference:

Aus. Pat. No. 6,794,700.
Aus. Pat. No. 9,013,101.
Aus. Pat. No. 9,013,201.
Aus. Pat. No. 9,013,401.
Butler et al., *Cancer Res.,* 60:5165–5170, 2000.
Butler et al., *Clin. Cancer Res.,* 7:962–970, 2001.
Chien et al., *Ann. Rev. Physiol.,* 55, 77–95, 1993.
Coffey et al., *Cancer Res.,* 61:3591–3594, 2001.
Durand et al., *Ann. Med.,* 27:311–317, 1995.
Eur. Pat. No. 1,123,111.
Eur. Pat. No, 1,170,008.
Eur. Pat. No. 1,173,562.
Eur. Pat. No. 1,174,438.
Eur. Pat. No. 1,208,086.
Eur. Pat. No. 1,233,958.
Furumai et al., *Cancer Res.,* 62:4916–21, 2002.
Gao et al., *J. Biol. Chem.,* 277:25748–55, 2002.
Gottlicher et al., *EMBO J.,* 20:6969–78, 2001.
Grozinger et al., *Proc. Natl. Acad. Sci. USA,* 96:4868–4873, 1999.
Han et al., *Cancer Research,* 60:6068–6074, 2000.
Hinnebusch et al., *J. Nutr.,* 132:1012–7, 2002.
Hoffinann et al., *Bioconjugate Chem.,* 12:51–55, 2001.
Japanese Patent Application No. 2001/348340.
Jones et al., *J. Clin. Invest.,* 98:1906–1917, 1996.
Jung, *Curr. Med. Chem.,* 8:1505–11, 2001.
Jung et al., *J. Med. Chem.,* 42:4669–4679, 1999.
Jung et al., *Med. Chem. Lett.,* 7:1655–1658, 1997.
Kao et al., *Genes Dev.,* 14:55–66, 2000.
Katoh et al., *J. Biol. Chem.,* 273:1511–18, 1998.
Kim et al., *Oncogene,* 18:2461–2470, 1999.
Kitazono et al., *J. Clinical Endoc. Metabol.,* 86(7): 3430–3435, 2001.
Komastsu et al., *Cancer Res.,* 61:4459–4466, 2001.
Kramer et al., *Trends in Endoc. Metabolism,* 12)7):294–300, 2001.
Lu et al., *Proc. Natl Acad. Sci. USA,* 97:4070–4075, 2000.
Mai et al., *J. Med. Chem.,* 45:1778–1784, 2002.
Marks et al., *J. Natl. Cancer Inst.,* 92(15):1210–1216, 2000.
Marks et al., *Clin. Cancer Res.,* 7:759–760, 2001.
Massa et al., *J. Med. Chem.,* 44:2069–2072, 2001.
McKinsey et al., *Proc. Natl. Acad. Sci. USA,* 97:14400–14405, 2000a.
McKinsey et al., *Nature,* 408:106–111, 2000b.
Molkentin et al., *Cell,* 93:215–228, 1998.
PCT Application No. WO 84/03564.
PCT Application No. WO 01/14581.
PCT Application No. WO 01/18045.
PCT Application No. WO 01/38322.
PCT Application No. WO 01/42437.
PCT Application No. WO 01/70675.
PCT Application No. WO 02/26696.
PCT Application No. WO 02/26703.
PCT Application No. WO 02/30879.
PCT Application No. WO 02/46129.
PCT Application No. WO 02/46144.
PCT Application No. WO 02/50285.
PCT Application No. WO 02/51842.
Remington's Pharmaceutical Sciences, 15$^{th}$ ed., pages 1035–1038 and 1570–1580, Mack Publishing Company, Easton, Pa., 1980.
Sadoshima and Izumo, *Ann. Rev. Physiol.,* 59:551–571, 1997.
Saunders et al., *Cancer Res.,* 59–399–409, 1999.
Su et al., *Cancer Res.,* 60:3137–3142, 2000.
Takahashi et al., *Antibiotics,* 49:453, 1996.
Taunton et al., *Science,* 272:371, 1996.
Tong et al., *Nucleic Acids Res.,* 30:1114–23, 2002.
U.S. App. 2002/61860.
U.S. App. 2002/65282.
U.S. App. 2002/103192.
Van den Wyngaert et al., *FEBS Lett.,* 478:77–83, 2000.
Vigushin et al., *Anticancer Drugs,* 13:1–13, 2002.
Vigushin et al., *Cancer Res.,* 5(Suppl), 1999.
Vigushin et al., *Clinical Cancer Res.,* 7:971–976, 2001.
Workman and Kingston, *Annu. Rev. Biochem.,* 67:545–579, 1998.
Yamano et al., Amer. Soc. Gene Ther., 2000.
Young et al., Handbook of Applied Therapeutics, 7.1–7.12 and 9.1–9.10, 1989.
Zhou et al., *Proc. Natl. Acad. Sci.,* 98:10572–10577, 2001.

What is claimed is:

1. A method of treating heart failure comprising:
    (a) identifying a patient having heart failure; and
    (b) administering to said patient a histone deacetylase inhibitor.

2. The method of claim 1, wherein said histone deacetylase inhibitor is selected from the group consisting of trichostatin A, trapoxin B, MS 275-27, m-carboxycinnamic acid bis-hydroxamide, depudecin, oxamfiatin, apicidin, suberoylanilide hydroxamic acid, Scriptaid, pyroxamide, 2-amino-8-oxo-9,10-epoxy-decanoyl, 3-(4-aroyl-1H-pyrrol-2-yl)-N-hydroxy-2-propenamide and FR901228.

3. The method of claim 1, wherein administering comprises intravenous administration of said histone deacetylase inhibitor.

4. The method of claim 1, wherein administering comprises oral, transdermal, sustained release, suppository, or sublingual administration.

5. The method of claim 1, further comprising administering to said patient a second therapeutic regimen.

6. The method of claim 5 wherein said second therapeutic regimen is selected from the group consisting of a beta blocker, an iontrope, diuretic, ACE-I, AII antagonist, and $Ca^{++}$-blocker.

7. The method of claim 5, wherein said second therapeutic regimen is administered at the same time as said histone deacetylase inhibitor.

8. The method of claim 5, wherein said second therapeutic regimen is administered either before or after said histone deacetylase inhibitor.

9. The method of claim 1, wherein treating comprises improving one or more symptoms of heart failure.

10. The method of claim 9, wherein said one or more symptoms comprises increased exercise capacity, increased blood ejection volume, left ventricular end diastolic pressure, pulmonary capillary wedge pressure, cardiac output, cardiac index, pulmonary artery pressures, left ventricular end systolic and diastolic dimensions, left and right ventricular wall stress, or wall tension, quality of life, disease-related morbidity and mortality.

* * * * *

UNITED STATES PATENT AND TRADEMARK OFFICE
CERTIFICATE OF CORRECTION

PATENT NO. : 6,946,441 B2  Page 1 of 1
DATED : September 20, 2005
INVENTOR(S) : Long et al.

It is certified that error appears in the above-identified patent and that said Letters Patent is hereby corrected as shown below:

Column 25,
Line 61, delete "oxamfiatin" and insert -- oxamflatin --.

Signed and Sealed this

Fourth Day of April, 2006

JON W. DUDAS
*Director of the United States Patent and Trademark Office*

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:

-continued

```
<223> OTHER INFORMATION: Description of Artificial Sequence:  Synthetic
      Primer

<400> SEQUENCE: 1
ccgaggccag ttgagatcag tc                                              22

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
aatgtgacca agctgcgtga cacaccacaa gggcttagga tcttttgcga tctgctcaag     60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
tggagcaaaa cagaatggct ggctttaatg cttcaagttt tccatttcct ttccacaggg     60

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
cgaacgttta tgtttattgt ggattggcca cagcgagggt ctgctggaga gg             52

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
gctttattct gcttccacct aaagggctgt tgcaaaggct ccaggtctga gggcttc        57
```